United States Patent [19]
Black et al.

[11] Patent Number: 6,130,900
[45] Date of Patent: Oct. 10, 2000

[54] PULSED INTRACAVITY FREQUENCY-CONVERTED SOLID-STATE LASER WITH LONG-PULSE SIMULATION

[75] Inventors: John F. Black, San Mateo; George Frangineas, Fremont; Hartmuth Hecht, Moss Beach, all of Calif.

[73] Assignee: Coherent, Inc., Santa Clara, Calif.

[21] Appl. No.: 09/263,338

[22] Filed: Mar. 5, 1999

[51] Int. Cl.[7] ........................................... H01S 3/10
[52] U.S. Cl. ................................. 372/25; 372/22; 372/93
[58] Field of Search .................................. 372/25, 22, 92, 372/93

[56] References Cited

U.S. PATENT DOCUMENTS

| | | | |
|---|---|---|---|
| 5,272,713 | 12/1993 | Sobey et al. | 372/25 |
| 5,406,577 | 4/1995 | Gagosz | 372/69 |
| 5,642,370 | 6/1997 | Mitchell et al. | 372/25 |
| 5,871,479 | 2/1999 | Furumoto et al. | 606/9 |

FOREIGN PATENT DOCUMENTS

| | | | |
|---|---|---|---|
| 2218660 | 11/1989 | United Kingdom | B23K 26/00 |
| WO 97/37602 | 10/1997 | WIPO | A61B 17/41 |

OTHER PUBLICATIONS

T.H. Jeys, A.A. Brailove & Mooradian, "Sum fequency generation of sodium resonance radiation," *Applied Optics*, vol. 28, No. 13, Jul. 1, 1989, pp. 2588–2591.

*Primary Examiner*—Leon Scott, Jr.
*Attorney, Agent, or Firm*—Limbach & Limbach L.L.P.

[57] ABSTRACT

In an intracavity frequency-converted pulsed laser, output-pulses having a duration longer than three milliseconds are simulated by a burst of temporally spaced-apart pulses having a shorter duration, the burst duration being about equal to the duration of the pulse being simulated. In an example of the laser including a KTP crystal providing frequency-doubling and having an Nd:YAG gain-medium for providing fundamental radiation at a wavelength of 1064 nm, a thin-etalon having a thickness of about 75 micrometers is included in the laser cavity to suppress generation of laser-radiation at wavelengths of 1061 and 1074 nm. Suppression of oscillation at these wavelengths prevents damage in the KTP crystal due to abrupt intracavity power surges thereby preventing damage to the KTP crystal. Examples of intracavity-pumped optical parametric oscillators including a thin etalon and operated in a similar manner are also disclosed.

20 Claims, 6 Drawing Sheets

PULSED INTRACAVITY FREQUENCY-CONVERTED SOLID-STATE LASER WITH LONG-PULSE SIMULATION

TECHNICAL FIELD OF THE INVENTION

The present invention relates to intracavity frequency-converted, pulsed, solid-state lasers for repetitively delivering long output-pulses having a pulse duration in a range from about three milliseconds (ms) to tens of milliseconds. The invention relates in particular to such a laser wherein repeatedly-delivered output-pulses are replaced by repeatedly delivered bursts (trains or groups) of pulses of shorter duration, each burst having about the same duration as the long output-pulse being replaced.

DISCUSSION OF BACKGROUND ART

Repetitively-pulsed lasers having a pulse duration in the range of tens of milliseconds are preferred in a number of laser surgical treatments, both therapeutic and cosmetic. By way of example, such lasers are useful in non-ablative treatments of biological tissue. Such treatments include removal of heavily pigmented skin lesions, such as so-called port-wine stains. A preferred wavelength is a wavelength in the yellow-green region of the spectrum, for example, in a wavelength range between about 500 and 600 nanometers (nm). Long pulse operation allows the delivery of relatively high energy at relatively low peak intensity. This avoids complications due to epidermal damage and microvaporization of blood in vessels. These kinds of treatments are preferably provided by a laser beam extending over a relatively broad area, for example, from about two to ten or more millimeters in diameter. Generally, in such broad area treatments, the larger the area-per-pulse that can be effectively treated, the shorter will be the treatment time and cost, and the deeper will be the penetration of energy and therapeutic fluences.

The area that can be treated in a single pulse is determined, among other considerations, by the energy density (energy-per-unit-area) in the treatment beam required for effective treatment. Accordingly, the higher the absolute energy-per-pulse available in a laser, the broader the area over which it can be distributed at a particular energy density.

Pulse-repetition rate for treatment is preferably greater than 1 Hz. At a slower rate, a surgeon may be required to wait an inordinately long time between an irradiation of one area and an adjacent area. At faster rates, it becomes possible to treat larger areas by moving the treatment beam quasi-continuously.

Considering the above-discussed factors, in designing a laser for pulsed broad-area surgical treatment, an important consideration is simply devising an arrangement for driving the laser, stably, as hard as possible, and as efficiently as possible to provide the fastest areal treatment rate per unit cost (capital and operating) of the laser.

A preferred laser type for providing radiation in the green region of the visible spectrum is an intracavity frequency-doubled solid-state laser wherein a gain-medium such as Nd:YAG provides a fundamental wavelength (1064 nm for Nd:YAG) in the near-infrared (NIR) spectral region. The NIR radiation is frequency-doubled in an optically-nonlinear crystal such as KTP (potassium titanyl phosphate) to provide output-radiation at half the fundamental wavelength (532 nm). Yellow (589 nm) radiation may be generated by intracavity sum-frequency generation by mixing 1064 nm and 1319 nm Nd:YAG radiation.

Operating a pulsed solid-state laser at a pulse duration of tens of milliseconds at relatively low peak power is inherently inefficient, frequency multiplication notwithstanding. At low peak powers second harmonic conversion requires an extremely low loss (<0.5% per round trip) cavity for the fundamental wavelength. The inefficiency problem is further exacerbated as frequency-multiplication or other frequency conversion in optically-nonlinear media, in itself, is an inherently inefficient process.

There is a need to improve efficiency of long pulse intracavity frequency-converted lasers for medical applications. Means of improving such efficiency, of course, should preferably be consistent with above-described medical considerations for optimum pulse-length and energy.

SUMMARY OF THE INVENTION

The present invention addresses the above-discussed efficiency problem of an intracavity frequency-converted long pulse, solid-state laser operation. The problem is overcome, inter alia, by substituting for a single, long pulse, a burst of shorter pulses, the overall burst being of about the same duration as the single long pulse. By operating in this way, it is possible to provide more total energy in a burst duration than could be achieved in a single long pulse of the same duration in a similarly configured laser. This mode of operation is referred to hereinafter as "burst-mode" operation.

An increase in efficiency of generating fundamental radiation by operating in the burst-mode can be anticipated from a simple consideration that individual pulses in a burst have a higher peak power than would the single long pulse, thereby providing that a bigger percentage of pump-power delivered to the gain-medium is above the lasing threshold in a laser resonator. An unexpected advantage is that burst-mode operation provides a significant increase in real efficiency of conversion of the fundamental (NIR radiation) to output (green) radiation, and furthermore at burst durations less than that at which burst-mode operation provides any significant efficiency-advantage, compared with an equivalent long-pulse in generating fundamental radiation.

In one aspect of the present invention, a pulsed intracavity frequency-converted, solid-state laser, comprises a first resonant-cavity including a solid-state gain-medium. An optical-pump is provided for energizing the solid-state gain-medium, thereby causing laser-radiation at a fundamental wavelength to circulate in said first resonant-cavity. An optically-nonlinear crystal is located in the resonant-cavity for converting the frequency of the laser-radiation, thereby providing output-radiation having a wavelength different from that of the fundamental wavelength. The first laser-resonant-cavity is arranged such that said laser-radiation circulates in more than one longitudinal mode, and is operated in such a way that the frequency-converted output-radiation is provided in repeated bursts of output-pulses at a burst-repetition rate between about 1 Hz and 5 Hz. Each of the bursts has a duration greater than about 3 ms and includes two or more output-pulses having a duration between about 0.5 and 4.0 ms.

The optically-nonlinear crystal can be selected and arranged to double the frequency of the laser-radiation, such that the output-radiation has a wavelength half of that of the fundamental radiation. Alternatively, the optically-nonlinear crystal can be selected and arranged to convert the laser-radiation into radiation having a signal-component and an idler-component, both of which components have a frequency different from the frequency of said laser-radiation.

The signal-component provides the output-radiation. The optically-nonlinear crystal can also be used to mix the fundamental frequency with a second (different) fundamental frequency generated by a second gain-medium in a second resonant cavity cooperative with the first resonant cavity.

In another aspect of the present invention, in which the gain-medium provides optical gain at at least first and second wavelengths and the optically nonlinear crystal is arranged to convert radiation at the first wavelength, an etalon is located in the resonant-cavity. The etalon is configured to have a reflectivity sufficiently low for the first wavelength and sufficiently high for the second wavelength that, on energizing the gain-medium, only laser-radiation of the first wavelength circulates in the resonant-cavity. This provides that the optically-nonlinear crystal is not damaged by intracavity power surges which would occur were laser-radiation of the second wavelength generated in preference to laser-radiation of the first wavelength.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the invention.

DETAILED DESCRIPTION OF THE INVENTION

Figure 1:
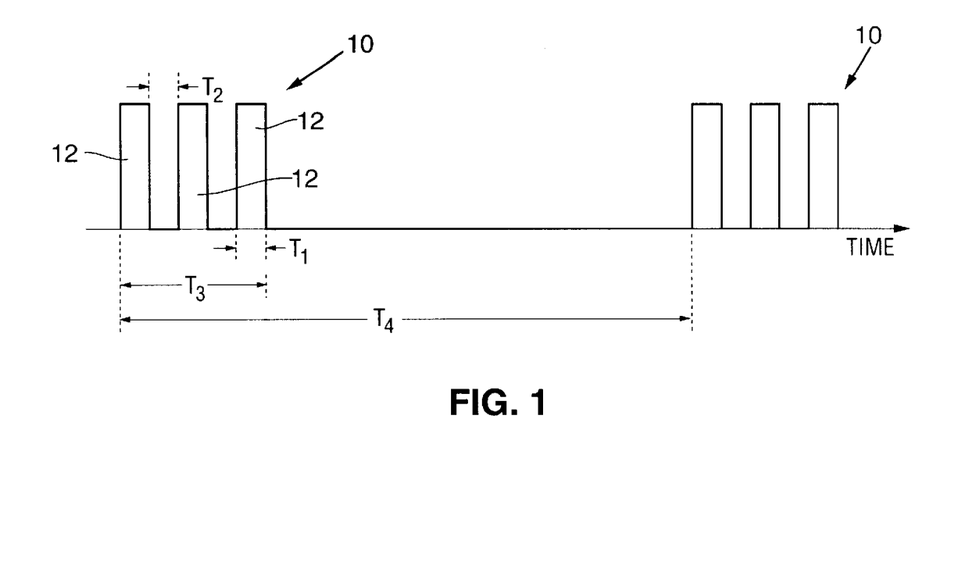
FIG. 1 is a graph schematically illustrating a series of bursts of pulses delivered by a pulsed solid-state laser in accordance with the present invention

Turning now to the drawings, wherein like components are designated by like reference numerals, FIG. 1 schematically depicts a burst 10 of three pulses 12 of laser-radiation. Pulses 12 have a duration $T_1$ and are separated by a time interval $T_2$, resulting in a burst duration $T_3$. In operation of a pulsed solid-state laser in accordance with the present invention bursts 10 are repeatedly delivered at a time interval therebetween of $T_4$. Burst 10 is arranged to provide a clinical effect similar to a single pulse having the same duration as the burst. As summarized above, the burst-mode operation in accordance with the present invention provides that more laser-radiation energy can be delivered in time $T_3$ than could be delivered in a single pulse of the same duration.

A pulse 12 preferably has a duration of at least 0.5 ms, but preferably not longer than about 50 ms. This is because the pulse must be long enough to avoid peak power exceeding a tissue-damage threshold, but not sufficiently long that the thermal relaxation time of biological material being treated is exceeded, thereby causing non-selective damage to adjacent tissue or cells. By way of example such non-selective damage may include epidermal/dermal separation; epidermal devitalization, and blood vessel damage due to microvaporization of blood purpura. Maintaining burst duration less than the thermal relaxation time of tissue also avoids triggering pain receptors be excessive thermal diffusion, thereby causing a patient being treated to feel pain.

Interval $T_4$ is preferably less than about 1 second, providing a burst repetition-rate of about 1 Hz or greater. This is important in treating an area of tissue which has a larger area than the treatment beam, requiring that the treatment beam be moved about the treatment area to make sure all of that area is treated. As noted above, at a burst-repetition rate slower than 1 Hz, a surgeon may be required to wait an inordinately-long time between irradiation of tissue in one area and an adjacent area. At faster rates, it becomes possible to overlap irradiation areas while moving the treatment beam quasi-continuously, thereby achieving a more uniform treatment. Burst-repetition rate is preferably no faster than about 5 Hz. A faster rate would be difficult for a surgeon to control.

Figure 2:
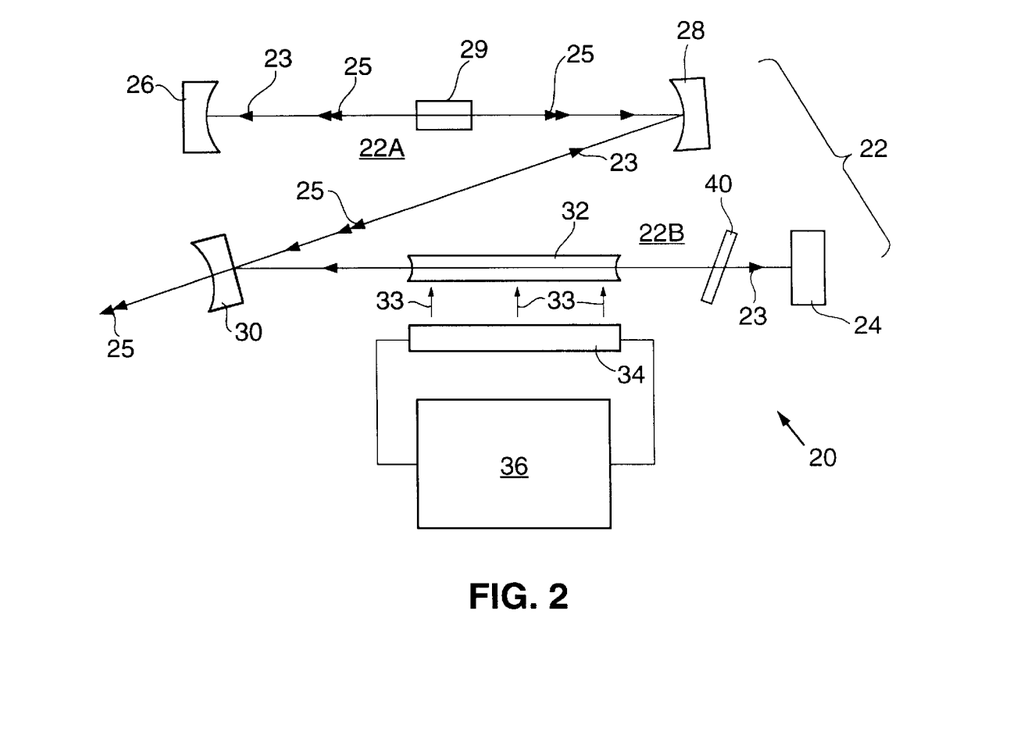
FIG. 2 shows one embodiment of a pulsed, intra-cavity frequency-doubled, Nd:YAG laser in accordance with the present invention including a thin-etalon to prevent generation of laser-radiation at wavelengths of 1061 nm and 1074 nm.

Referring now to FIG. 2, one preferred embodiment 20 of a laser in accordance with the present invention is illustrated. Laser 20 is a pulsed, intra-cavity frequency-doubled laser. Laser 20 includes a resonator 22, terminated by a plane mirror 24 and a concave mirror 26. Resonator 22 is "folded" into arms 22A and 22B by fold mirrors 28 and 30. Resonator arm 22B includes a gain-medium 32 which generates radiation at a fundamental frequency to be doubled. Resonator arm 22A includes an optically-nonlinear crystal 29 for doubling the frequency of the fundamental radiation. The path of fundamental and frequency-doubled radiation is indicated respectively by single arrows 23 and double arrows 25. Frequency-doubled light (output-radiation) 25 exits resonator 22 via mirror 30. In preferred embodiments of laser 20 for providing green-light by frequency-doubling NIR radiation, gain-medium 32 is preferably a Nd:YAG rod for generating fundamental radiation at 1064 nm. Other suitable neodymium doped gain media include Nd:YLF, Nd:YALO, Nd:SFAP, Nd:YAP and Nd:YAB.

As noted above, resonator arm 22A includes optically-nonlinear crystal 29 for frequency-doubling the fundamental radiation. In preferred embodiments of laser 20, including the Nd:YAG gain-medium, optically-nonlinear crystal 29 is preferably a critically-phase-matched, angle-tuned KTP crystal 29 for doubling the frequency of the 1064 nm laser-radiation (halving the wavelength to 532 nm) generated by rod 32. Other preferred materials for optically-nonlinear crystal 29 include LBO, BBO, CLBO, RTA, CTA, RTP, KTA, KNbO3, and LiNbO3.

In an embodiment of the inventive frequency-doubled laser wherein the gain-medium is Nd:YAG, laser mirrors 24 and 28 are coated for high reflectivity at both 532 nm and 1064 nm. Mirror 26 is coated for high reflectivity at 1064 nm. Mirror 30 is coated for high reflectivity at 1064 nm and high transmission at 532 nm. Rod 32 is optically pumped by radiation 33 from a flashlamp 34 driven by a power supply 36.

Resonator 22 is arranged for multiple longitudinal-mode operation, for maximum possible power-output, with beam quality being of secondary importance. As such, it does not contain any wavelength-selective elements having sufficient spectral resolution to force the resonator to operate in a single longitudinal-mode (single-frequency operation). Single frequency-operation is typically selected in-prior art lasers wherein beam quality is of far greater importance than output-power. Those skilled in the art will be aware that in some prior-art resonators a KTP optically-nonlinear crystal (in addition to providing frequency-doubling) is used in conjunction with other polarizing elements for limiting (by frequency selection in the manner of a Lyot filter) the number of longitudinal-modes which can be generated.

As discussed above, pulse-bursts of output-radiation, here at a wavelength of 532 nm, are delivered from resonator 22 at mirror 30. As noted above, the bursts may be generated by operating power supply 36 such that flashlamp 34 delivers pump-pulses in bursts corresponding to desired laser-pulse bursts.

A preferred power-supply 36 is a reservoir-capacitor type power supply. This type of power supply is preferred for the flashlamp-pumped resonator of laser 20. The power supply may be controlled to deliver pump-pulse bursts corresponding to desired laser-pulse bursts. This type of power-supply is well known to those skilled in the art to which the present invention pertains. A detailed description of such a power-supply is not necessary for understanding principles of the present invention. Accordingly a detailed description of such a power-supply is not presented herein.

It is pointed out here that principles of the present invention are not limited to a resonator in which a flashlamp is used as an optical pump. Optical-pumping may be provided, for example, by laser diode arrays, in which case a current regulated power supply would be preferred for driving the diode arrays.

Operating resonator 22 in the burst-mode can be anticipated to provide an increase in efficiency of generating fundamental radiation from a simple consideration of providing that a bigger percentage of pump-power delivered to the gain-medium is above the lasing threshold of the laser resonator. This increase in efficiency becomes significant at pulse durations of longer than about 10.0 ms. A problem that was encountered in designing an intracavity frequency-multiplied resonator in accordance with the present invention, however, was that even at a pulse length as short 10.0 ms, overall efficiency was only about one-half of that which might be expected from a simple product of efficiency of generating fundamental radiation and steady state conversion efficiency of the optically-nonlinear crystal. This difference is attributed to loss of a proper phase-matching condition in optically-nonlinear crystal 29 and occurred at the high pump-power necessary to provide the high output-power, for example, greater than about 25 Watts (W) peak power, contemplated for lasers in accordance with the present invention. The loss of phase-matching results in a reduction in conversion efficiency. The loss of phase-matching is due to absorption of fundamental radiation and can be explained briefly and generally as follows.

In the optically-nonlinear crystal, for optimum conversion efficiency of a fundamental beam into a second-harmonic beam, the crystal must be arranged such that the fundamental and the second-harmonic beam generated thereby remain in phase as they traverse the crystal. This is arranged, inter alia, by orienting a particular crystallographic plane of the optically-nonlinear crystal at a particular angle to the fundamental beam, and by maintaining the crystal at a fixed temperature. Maintaining the crystal at a fixed temperature is most often accomplished by locating the crystal in an oven which is maintained at some fixed temperature above a highest-anticipated ambient temperature.

At the high output-power levels of a laser in accordance with the present invention, even in pulses only as long as 10 ms, transient heating-effects due to absorption of pulses of fundamental radiation in the optically-nonlinear crystal can lead to significant loss of conversion efficiency (accordingly overall efficiency) due to a resulting loss of phase-matching. Loss of phase-matching is referred to alternatively hereinafter as "dephasing"

Figure 3:
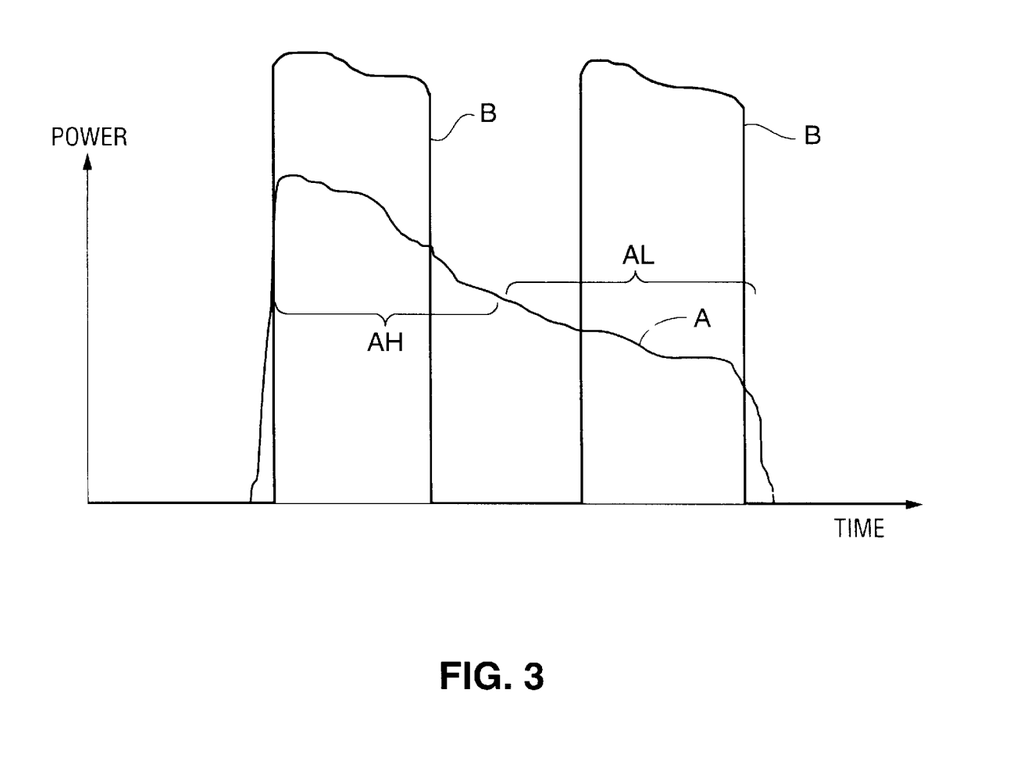
FIG. 3 is a graph schematically illustrating the general form of power loss during a ten-millisecond frequency-doubled pulse due to progressive loss of phase-matching, compared with essentially equal power being maintained in two three-millisecond pulses separated by about three-milliseconds and having collectively about the same energy as the ten millisecond pulse.

It is believed, without being limited to a particular theory, that as doubling-efficiency (conversion-efficiency) is decreased, residual NIR power circulating in resonator 22 is greater. Accordingly, when the optically-nonlinear crystal absorbs the NIR (fundamental) radiation and heats-up, dephasing occurs, and conversion-efficiency is reduced. Reduction in conversion efficiency, in turn, leads to increased NIR power circulation and heating and further dephasing. It was found in attempting to operate with a single 10 ms pulse that considerable end-of-pulse peak-power droop resulted as the crystal dephased through overheating. This is depicted schematically in FIG. 3 as curve A. Apart from a simple loss of conversion efficiency, this dephasing phenomenon could lead to a portion (AH) of the pulse being sufficiently energetic to be of therapeutic value while a portion (AL) of the pulse was insufficiently energetic to be of therapeutic value. This could create problems in controlling radiation dosage for a patient. Using a "burst" of two 3 ms pulses, separated by 3 ms, in accordance with the present invention (curve B), to provide the same green output-radiation energy (in total), the optically-nonlinear crystal absorbed less circulating IR, heated up less, and accordingly did not dephase as fast. In this operation-mode, energy in the each pulse was about the same. It should be noted here that curves A and B of FIG. 3 provide only a schematic general representation of the dephasing problem and its solution. A more detailed analysis of actual pulses is provide further hereinbelow.

In an intracavity frequency-doubled laser in accordance with the present invention, burst-mode operation can provide in a 10 ms burst of pulses about two or more times the efficiency of generating frequency-doubled radiation than would be achieved in a similar resonator for a single 10 ms pulse. Further a significant increase in efficiency of generation of frequency-doubled radiation can be expected from burst-mode simulation of pulses as short as about 5.0 ms, and even as short as 3 ms.

Another problem that was discovered in operating in the burst-mode at high, intracavity, pulse-power (pulse-power, here, referring to power of individual pulses in a burst) was that fundamental radiation could also be generated in the Nd:YAG gain-medium at wavelengths of 1061 nm and 1074 nm. This can be accompanied by intracavity power "spiking" which can cause damage to the doubling-crystal and result in power instability and, in particular, "drop-outs" or abrupt and drastic reductions in output-power in pulses within a burst. These drop-outs, in turn, cause the intracavity NIR power to abruptly increase to the point where the crystal can be damaged. Damage to the crystal can be damage to the crystal itself or to any antireflection coatings on the crystal. Damage may also occur at other coatings such as those on resonator end mirrors or fold mirrors. Typically at these high peak output-powers catastrophic doubling crystal damage was observed at the onset of power drop-outs. These problems began to be encountered when attempting to provide frequency-doubled (green) output power greater than about 25.0 W peak power and were consistently encountered when attempting to provide peak frequency-doubled (green) output-power greater than about 50.0 W peak power. One explanation for this is as follows.

The primary loss mechanism for laser 20 is frequency-doubling of the 1064 nm to 532 nm light. Crystal 29 is angle-tuned to achieve this frequency-doubling. The laser would prefer not to have this loss mechanism, and tries to find a way to reduce its losses. It can achieve this by jumping to (lasing at) one or both of wavelengths at 1061 nm and 1074 nm which are not frequency-doubled by optically-nonlinear crystal 29. This 1061 and 1074 nm lasing may be described as parasitic oscillation or generation of parasitic radiation. In the absence of a means for preventing this parasitic oscillation, the 1074 nm wavelength oscillates almost continuously for all or some substantial fraction of a pulse duration, and constitutes a simple, albeit problematical, loss of available green output-power. The 1061 nm line "hops" rapidly in and out of oscillation in a chaotic manner during a pulse. It is believed, without being limited to a particular theory, that this 1061 nm rapid "wavelength-hopping" causes the above discussed NIR power spiking and resulting damage to optically-nonlinear crystal 29.

Figure 4:
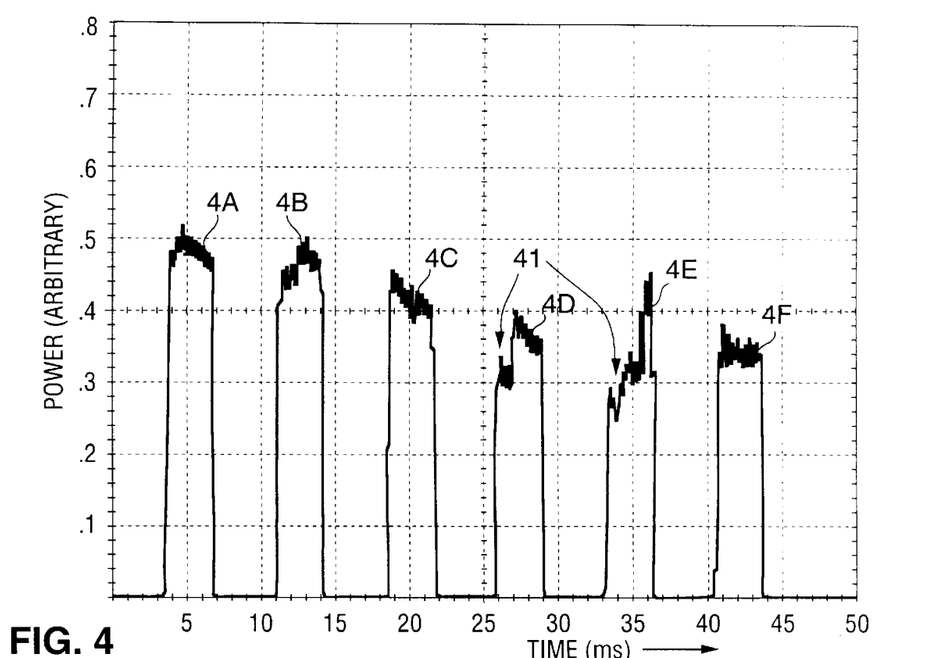
FIG. 4 is a graph schematically illustrating an oscilloscope measurement showing general power reduction and abrupt power fluctuation in a 40 ms burst of six 3 ms pulses from a laser configured generally as depicted in FIG. 2 but from which the thin-etalon has been omitted.

By way of example, FIG. 4 graphically depicts, for one example of a laser 20, without etalon 40, wherein gain-medium 32 is Nd:YAG and optically-nonlinear crystal 29 is KTP, a representation of an actual oscilloscope trace of power as a function of time of a 40 ms long burst of six green-light (532 nm) pulses each of about 3 ms duration.

It can be seen that peak pulse power drops continuously from the first pulse (pulse 4A) to the last pulse (pulse 4F) in the burst as a result of dephasing and increasing parasitic oscillation of the 1074 nm wavelength. Further it can be seen that in certain pulses, in particular pulses 4D and 4C, there is an abrupt drop, in green-light output power, as indicated by arrows 41, immediately after generation of green light begins . It is believed that during such an abrupt drop in green-light output power, there is a corresponding surge in NIR power circulating in resonator 22. During such a surge in NIR power, depending on actual pump-power and on the material of optically-nonlinear crystal 29, there is a relatively-high probability of damage to optically-nonlinear crystal 29. Certain optically-nonlinear materials such as KTP, KTA, CTA and RTP are particularly susceptible to such damage. It is believed that portion the abrupt power drops and generally "noisy" behavior of pulses 4D and 4E is attributable to above described wavelength hopping at 1061 nm wavelength.

Figure 5A:
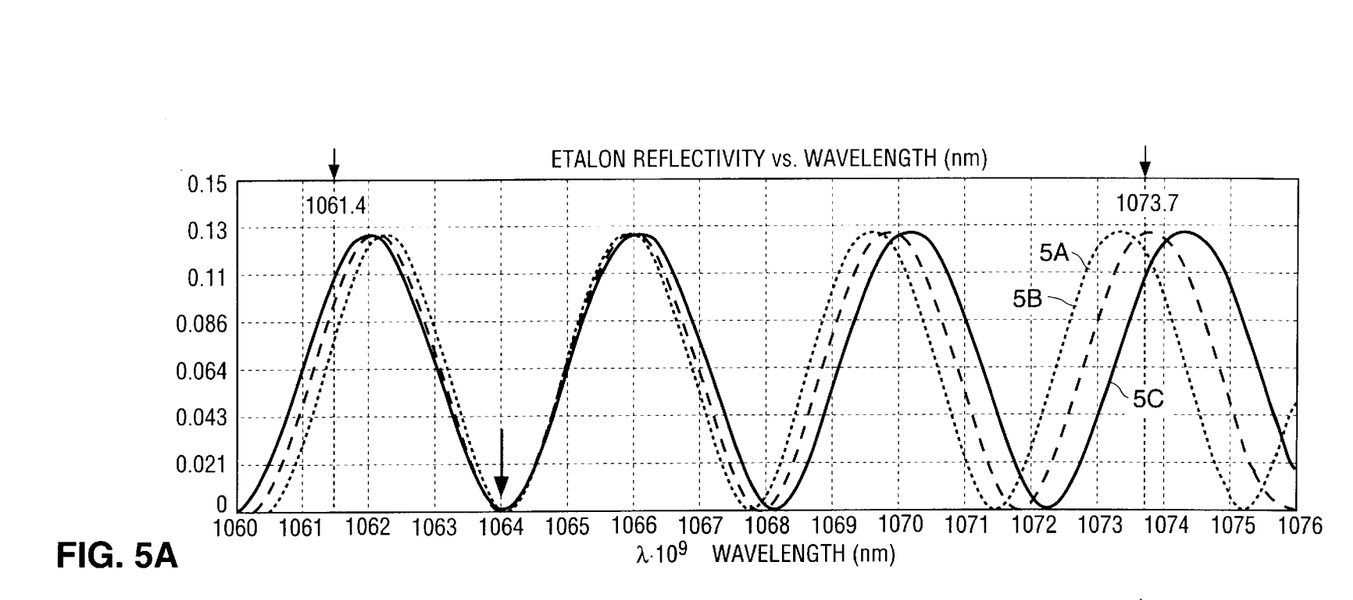
FIG. 5A is a graph schematically illustrating computed reflection as a function of wavelength at for one example of the thin-etalon of FIG. 2 having a thickness of 100±5 micrometers.

A solution to above-described problems due to generation of parasitic radiation at 1061 and 1074 nm is to insert, in resonator 22, the thin-etalon 40 which is tuned to allow passage of 1064 nm radiation, but which has a free-spectral-range (FSR) and finesse arranged such that attenuation losses for 1061 nm and 1074 nm radiation are sufficient to prevent lasing even at the high peak pump-power. This can be achieved by an uncoated etalon. A preferred thickness for such an etalon is about 100.0 micrometers ($\mu$m). In FIG. 5A is depicted, graphically, reflectivity as a function of wavelength for uncoated etalons of fused-silica having thicknesses of 105.0, 100.0 and 95.0 $\mu$m (Curves 5A–C respectively). The 105.0 and 95.0 $\mu$m thicknesses represent deviations from a nominal 100 $\mu$m thicknesses which might be expected in the manufacturing process for such etalons. In each case the etalon has been angle tuned such that fundamental wavelength 1064.1 nm is at a reflectivity minimum with the 1061 (more precisely, 1061.4) nm wavelength being located at about an adjacent shorter-wavelength reflection maximum, i.e., slightly more than half a free-spectral-range (FSR/2) from the fundamental. This provides that the 1074 (more precisely, 1073.7) wavelength is located proximate a second longer wavelength reflection peak (5FSR/2). Tuning angles for curves 5A–C are 2.3, 4.97, and 6.8 degrees respectively.

Figure 5B:
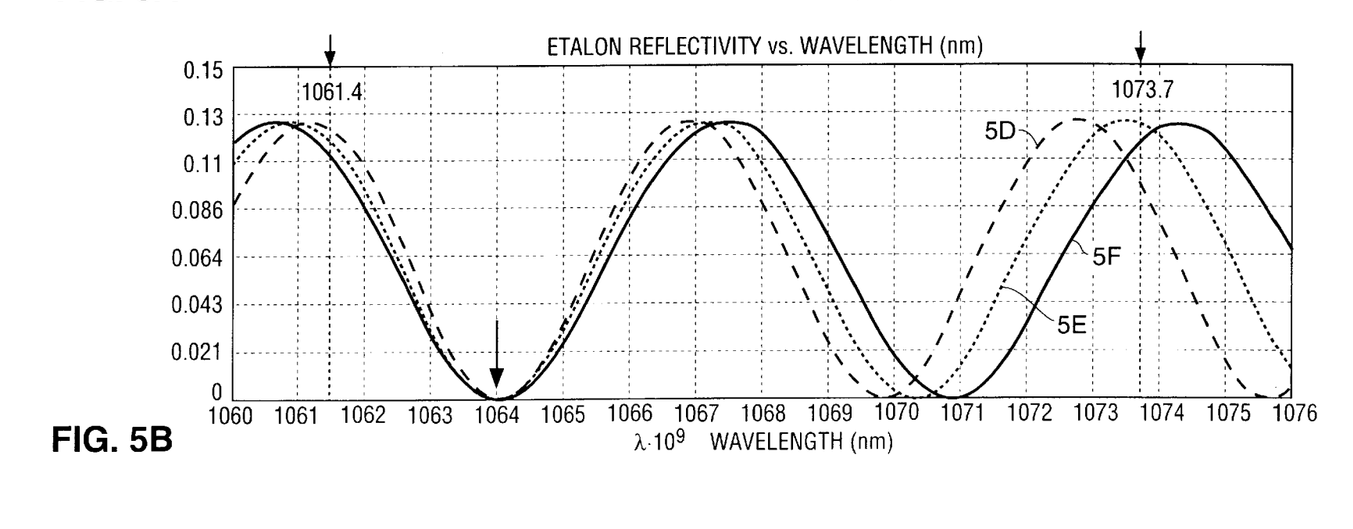
FIG. 5B is a graph schematically illustrating computed reflection as a function of wavelength at for one example of the thin etalon of FIG. 2 having a thickness of 62±5 micrometers.

In FIG. 5B is depicted, graphically, reflectivity as a function of wavelength for uncoated etalons of fused-silica having thicknesses of 67.0, 62.0 and 57.0 $\mu$m (Curves 5D–F respectively). The 67.0 and 57.0 $\mu$m thicknesses represent above-discussed deviations from a nominal 62.0 $\mu$m thicknesses. In each case, again, the etalon has been angle tuned such that fundamental wavelength 1064.1 nm is at a reflectivity minimum with the 1061.4 nm wavelength being located at about an adjacent shorter-wavelength reflection maximum, here, slightly less than FSR/2 from the fundamental. This provides that the 1073.7 nm wavelength is located proximate a second longer wavelength reflection peak (3FSR/2). Tuning angles for curves 5D–F are 6.55, 8.8, and 5.33 degrees respectively.

Clearly, for ensuring that only the 1064-nanometer oscillates or circulates in resonator 22, it is only necessary that reflectivity loss at about 1064 nm be sufficiently low to allow oscillation while being sufficiently high at about 1061 and 1071 nm to prevent oscillation at those wavelengths. An advantage, however, of arranging etalon 40 as described above is that the 1061, 1064 and 1074 wavelengths each lie on the etalon response-curve close to a maximum or minimum, about which are regions of least variation of reflection with wavelength. Because of this, effects variations in thickness due to manufacturing tolerances on selectivity are minimized . Further, the values of reflection at these wavelengths for any of the etalon thicknesses considered vary by less than about two-percent over about a 20° C. variation in ambient temperature. Accordingly, it is not necessary to provide a temperature controlled enclosure for the etalon. Particular advantages of an uncoated etalon are that it has a higher damage-threshold and lower polarization sensitivity to angle of incidence (tuning angle) than a coated etalon would have.

Clearly, there are other optical-thicknesses for etalon 40 which may provide sufficient selectivity to suppress laser action at the 1061 and 1074 wavelengths without those wavelength coinciding with reflection peaks. These can not be expected, however, to provide the same thermal tolerance of that selectivity as provided by the above-discussed example. Lack of thermal tolerance will become increasingly a problem if the etalon is made significantly thicker than 100 μm. Accordingly, it is preferable that etalon 40 should have a thickness no greater than about 250 μm.

It is emphasized, here, that etalon 40 should not be confused with etalons which are sometimes inserted in the cavity of frequency-doubled lasers to restrict operation of the laser to a single longitudinal mode from the closely-spaced (about 100 MHz, depending on cavity length) multiple longitudinal modes which are possible within the gain-bandwidth profile for the nominally 1064 nm radiation transition in the gain-medium. Such an etalon is typically very thick, for example on the order on several millimeters (mm) and would not be sufficient in itself to prevent laser action at 1061 and 1074 nm as described above. Those skilled in the art will recognize that while etalon 40 is described as limiting laser 10 to operation at only 1064 nm, the nominal 1064 nm operation is in the form of several axial or longitudinal modes having above-described closely-spaced frequencies within a bandwidth of several Gigahertz.

Figure 6:
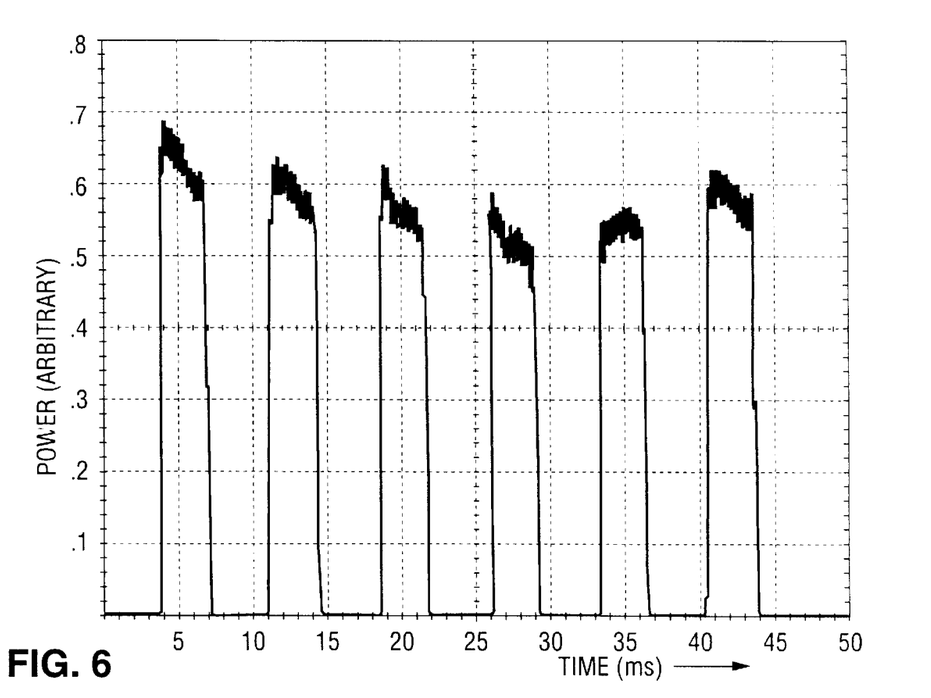
FIG. 6 is a graph schematically illustrating an oscilloscope measurement showing substantially reduced overall power loss, and elimination of abrupt power losses in a 40 ms burst of six 3 ms pulses from a laser configured generally as depicted in FIG. 2 in which the thin-etalon is included.

FIG. 6, depicts a representation of an actual oscilloscope trace of power as a function of time of a 40 ms long burst of six 532 nm 3 ms long output-pulses from a frequency-doubled Nd:YAG laser in accordance with laser 20 of FIG. 1, including the etalon 40, having a thickness of about 100 μm is arranged as depicted in FIG. 5A. All other operating conditions, including pump-power, are the same as for the pulse-burst example of FIG. 4.

It can be seen that the peak-power variation of pulses in the burst is significantly less than in the example of FIG. 4 and the power spiking within a pulse has been essentially eliminated. More dramatically however it can be seen that all pulses in the burst of FIG. 6 have a higher peak-power, for the same pump-power, than the most powerful pulse (pulse 4A) of the burst of FIG. 4. Total energy (radiation dose) in the burst of FIG. 6 is about 350% to 40% greater that the total energy in the burst of FIG. 4. This comparison of FIGS. 4 and 6 serves to illustrate that at the high peak-power levels (greater than 25 W) contemplated for lasers in accordance with the present invention, in the absence of any means to suppress parasitic oscillation, the parasitic oscillation would be a problem throughout the pulse-burst delivery. To reach the energy-per-burst of the burst of FIG. 6, pump-power level in the "no etalon" example would need to be increased by at least 400 and probably much more as the increased pump power would further exacerbate the parasitic oscillation problem.

A selection of pulse schedules of a laser operating in accordance with FIG. 1 is presented in TABLE 1. In this example of laser 20, gain-medium is Nd:YAG rod having a diameter of 4 mm and a length of 92 mm. Optically-nonlinear crystal 29 is a critically-phase-matched, angle-tuned KTP crystal having a length of about 5 mm and entrance and exit face dimensions about 3 mm×3 mm.

TABLE 1

| Burst Width (ms) | 15 | 20 | 30 | 40 | 50 |
|---|---|---|---|---|---|
| Max Energy (J/pulse) | 1.6 | 2.0 | 2.6 | 3.2 | 4.0 |
| Min Energy (J/pulse) | 0.7 | 0.8 | 1.0 | 1.2 | 1.6 |
| Max Rep-Rate (Hz) | 4.0 | 3.0 | 2.4 | 2.0 | 1.5 |
| Pulses per Burst | 3 | 3 | 4 | 6 | 7 |
| Pulse Width (ms) | 3.0 | 3.0 | 3.0 | 3.0 | 3.0 |
| Pulse separation (ms) | 3.0 | 5.5 | 6.0 | 4.4 | 4.8 |
| Average Power (W) | 6.4 | 6.0 | 6.2 | 6.4 | 6.0 |

TABLE 1 table is presented merely for guidance and should not be considered limiting. The table shows estimated energy delivered to tissue by a delivery system such as an optical-fiber or an articulated arm. Corresponding energy from a laser (delivered to the delivery system) would be about two times those of Table 1.

Figure 7:
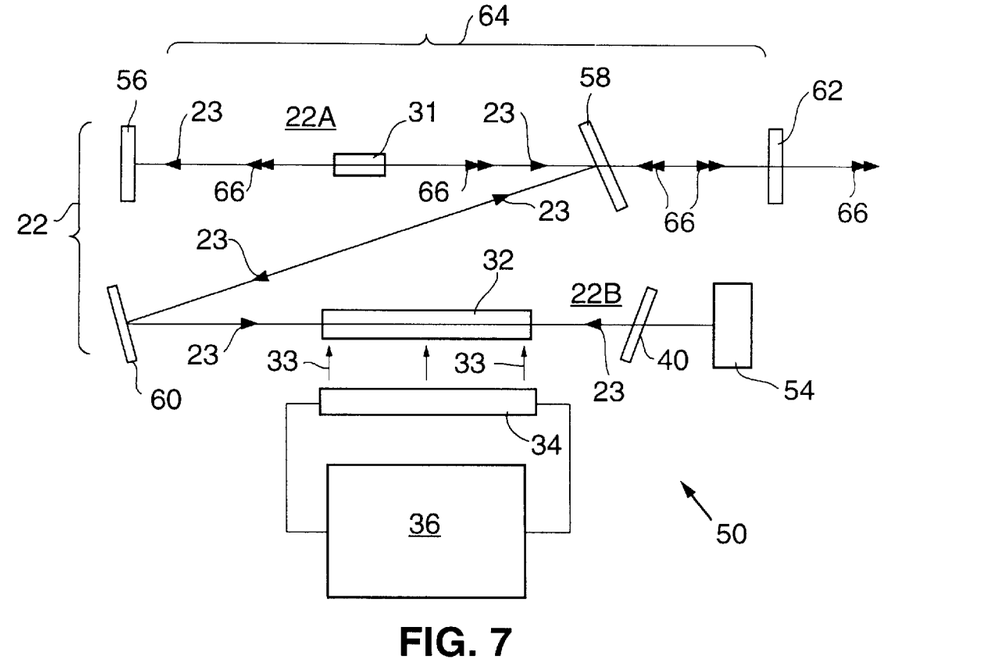
FIG. 7 schematically illustrates another embodiment of laser in accordance with the present invention arranged as a collinearly pumped optical parametric oscillator.

Continuing now with reference to FIG. 7, benefits of a laser in accordance with the present invention accruing from burst-mode operation and parasitic wavelength suppression can be realized if the laser is arranged (laser 50) as an optical parametric oscillator (OPO).

Optical parametric oscillators (OPOs) are based on the combination of an optically-pumped parametric gain-medium, which provides optical gain, disposed within an optical resonant-cavity. The parametric gain-medium is typically an optically-nonlinear crystal 31.

A parametric mixing process in the optically-nonlinear crystal provides gain by converting pump-light at a frequency $\omega_{pump}$ to light at optical-output frequencies $\omega_{signal}$ (signal light) and $\omega_{idler}$, according to the following expression.

$$\omega_{pump} = \omega_{signal} + \omega_{idler} \tag{1}$$

The optical resonant-cavity provides feedback of amplified signal-light which leads to sustained oscillation or resonating of the signal-light, and the production of usable signal-light output. The signal-light may be defined as laser-like light. It should be noted here that the designation "signal-light" is somewhat arbitrary. Two frequencies are generated any one of which may be selected as the signal the other, by default being the idler. Usually, but not necessarily, the higher frequency is selected for signal light.

The frequencies of the signal light and idler beams can be tuned over a wide range by adjusting angular alignment and/or temperature of the optically-nonlinear crystal, which affects the indices of refraction. The output frequencies are a function of the indices of refraction. OPOs are thus useful sources of tunable laser-like light. As in above-described laser 20, however, there must be proper phase-matching between the pump-light and signal light, and this phase-matching, at output powers contemplated for lasers in accordance with the present invention, may be adversely affected by the mechanisms described above for optically-nonlinear crystal 31. Likewise power fluctuation and crystal damage may be expected if pump-light is subject to above-described spurious wavelength changes.

Continuing with reference to FIG. 7, laser 50 includes a resonator 22 for fundamental radiation. Resonator 22 is formed between mirrors 56 and 54 and is folded into a "Z" configuration by mirrors 58 and 60. In one arm 22B of the resonator is included a (fundamental) gain-medium 32 pumped by light 33 from a flashlamp 34, energized by a power supply 36 as discussed above for laser 20. A thin etalon 40 is included in resonator arm 22B. In arm 22A of resonator 22 is located an optically-nonlinear crystal 31 serving as an optically-pumped parametric gain-medium as described above. Mirrors 54 and 60 of resonator 22 are coated for high reflectivity of fundamental radiation generated by gain-medium 32. Mirror 56 is coated for high reflectivity of fundamental radiation and of signal-light generated by interaction of the fundamental radiation with optically-nonlinear crystal 31. Mirror 58 is coated for high reflectivity of the fundamental radiation but for high transmission of the signal-light. Mirror 62 is partially reflective and partially transmissive for the signal light. Mirror 62 and mirror 56 form a resonator 64 for the signal light. The paths of fundamental radiation and signal-light are designated respectively by single arrows 23 and double arrows 66. Output-pulses of signal-light 66 are delivered from laser 50 via mirror 62.

Figure 8:
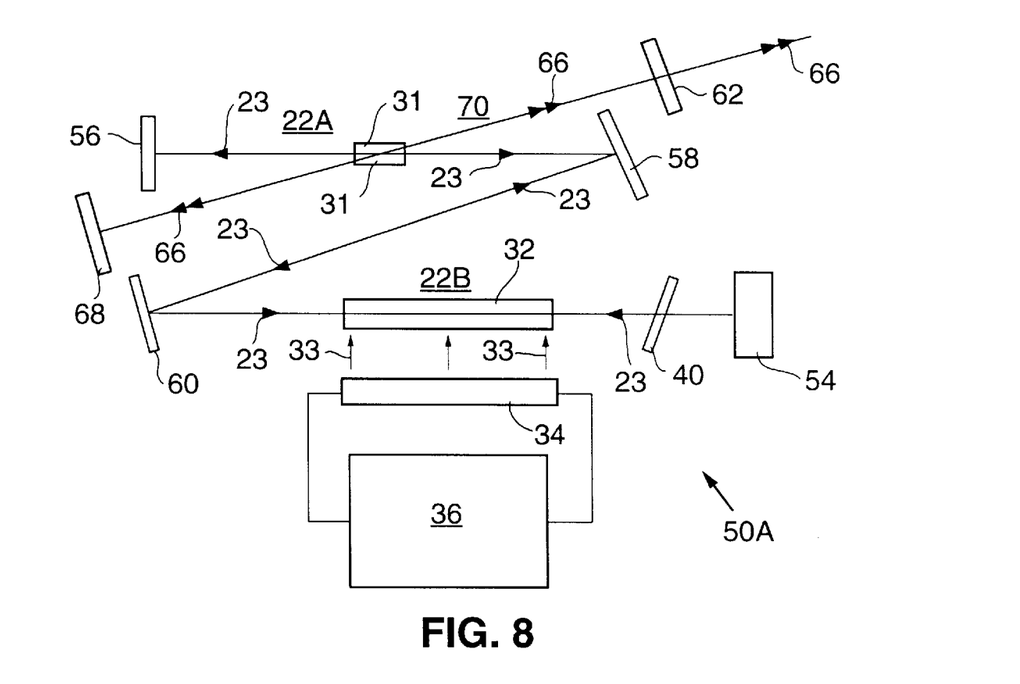
FIG. 8 schematically illustrates yet another embodiment of laser in accordance with the present invention arranged as a non-collinearly pumped optical parametric oscillator.

Laser 50 is illustrated as being arranged for collinear (with signal-light) pumping of optically-nonlinear crystal 31 by fundamental 23. Those skilled in the art will recognize that principles of the present invention are applicable in an arrangement wherein optically-nonlinear crystal is non-collinearly pumped. FIG. 8 depicts an OPO laser 50A arranged for non-collinear pumping. Laser 50A is similar in most respects to laser 50 but has mirror 62 arranged together with another mirror 68, to form a separate resonator 70 for signal light 66. Resonator 70 is arranged such that signal light 66 oscillates therein at an angle to pump-light 23 in resonator arm 22A of resonator 20. In laser 50A there is no requirement that mirror 58 be transparent to signal light.

Figure 9:
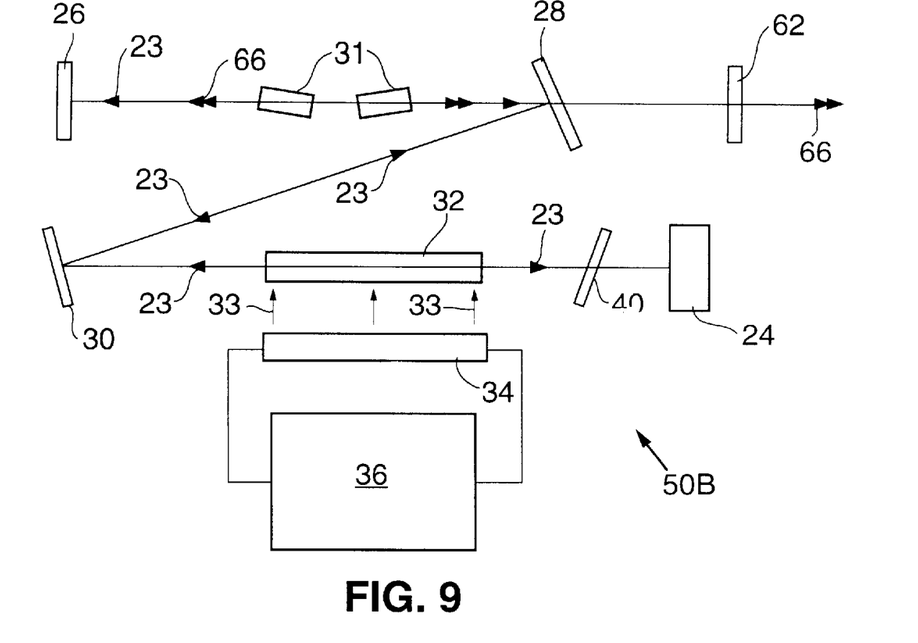
FIG. 9 schematically illustrates still another embodiment of laser in accordance with the present invention arranged as a collinearly pumped optical parametric oscillator, and including two optically-nonlinear crystals counter-inclined to each other with respect to the resonator axis to eliminate walk-off losses.

Referring now to FIG. 9 yet another OPO arrangement 50B of a laser in accordance with the present invention is illustrated. Here, laser 50B is similar to laser 50 of FIG. 7 with the exception that there are two optically-nonlinear crystals 31 included in arm 22A of resonator 22. Crystals 31 are arranged with corresponding axes thereof at an equal but opposite inclination to the resonator axis (as defined generally by the path of fundamental radiation 23). This is to compensate for "walk-off" (angular deviation between pump-light and signal light) losses which may result when only one such crystal is included.

Those skilled in the art to which the present invention pertains will recognize that such walk-off losses are not limited to the OPO arrangement of laser 50 but may also occur in a frequency-doubled laser in accordance with the present invention. Those skilled in the art will recognize accordingly without further illustration that a similar walk-off compensation is possible in an inventive frequency-doubled laser, for example, by including two oppositely-inclined optically-nonlinear crystals 29 in resonator-arm 22A of laser 20 of FIG. 2.

Figure 10:
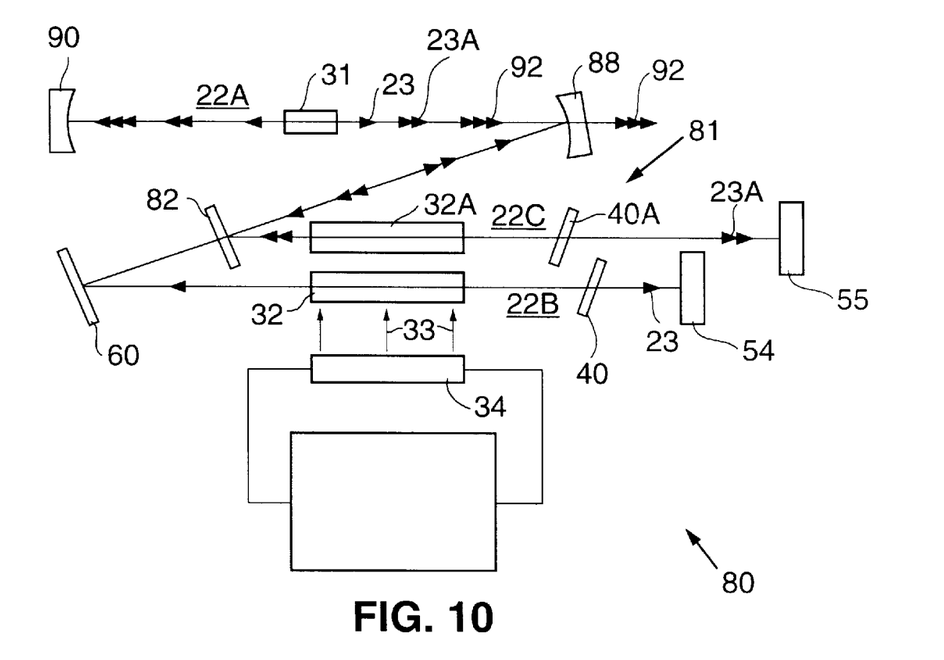
FIG. 10 schematically illustrates a further embodiment of laser in accordance with the present invention arranged for sum-frequency generation including two cooperative resonators each including a gain medium and an etalon and having a common section including an optically nonlinear crystal.

Referring now to FIG. 10, a preferred embodiment 80 of a laser in accordance with the present invention, arranged for sum-frequency generation, is depicted. Laser 80 includes a compound resonator 81 having a section 22A thereof, between focussing mirrors 88 and 90, including an optically-nonlinear crystal 31. A first branch 22B of resonator 81 is formed between mirrors 90 and 54 and is folded into a "Z" configuration by mirrors 88 and 60. Resonator branch 22B includes an Nd:YAG gain-medium 32 and a thin-etalon 40. Gain-medium 32 is pumped by pump-light 33 from a flashlamp 34 as described above for other inventive laser configurations. Etalon 40 is arranged to transmit 1064 nm radiation and reflect 1061 nm and 1074 nm radiation as described above.

A second branch 22C of resonator 81 is formed between mirrors 90 and 55 and is folded into a "Z" configuration by mirrors 88 and 82. Resonator branch 22C includes an Nd:YAG gain-medium 32A and a thin-etalon 40A. Gain-medium 32A is also pumped by pump light 33. This can be from the same flashlamp 34 using a suitable reflector configuration (not shown) or from a separate pump-light source (not shown). Etalon 40A is arranged to transmit 1319 nm radiation and reflect 1320 nm and 1334 nm radiation as described above.

Mirror 90 is coated for high reflection at ND:YAG fundamental wavelengths 1064 nm and 1319 nm, and their sum frequency wavelength of 589 nm. Mirror 88 is coated for high reflection at 1064 nm and 1319 nm, and high transmission at 589 nm. Mirror 82 is coated for high reflection at 1319 nm and high transmission at 1064 nm. Mirror 84 is coated for high reflection at 1319 nm. Mirrors 60 and 54 are coated for high reflectivity at 1064 nm. In this arrangement, fundamental radiation at 1319 nm oscillates in branch 22C of resonator 81 (see double arrows 23A); fundamental radiation at 1064 nm oscillates in branch 22B of resonator 81 (see single arrows 23); both fundamental wavelengths oscillate in common section 22A of resonator 81 and mix in optically nonlinear crystal 31 to provide sum-frequency radiation (triple arrows 92) which exits resonator 81 via mirror 88.

Above described inventive lasers in frequency-doubled (frequency-multiplied), OPO, or sum-frequency generator configuration may be collectively defined as intracavity "frequency-altered" lasers or intracavity "frequency-converted" lasers inasmuch as each includes a resonator for generating radiation at a first (fundamental) wavelength, and includes at least one optically-nonlinear crystal which provides (output) radiation at a different, second wavelength in response to passage therethrough of radiation of the first and any other fundamental wavelength. Frequency-multiplied radiation provided by a frequency-multiplied laser in accordance with laser 20 of FIG. 2; signal-light provided by any of the intracavity OPO arrangements of FIGS. 7, 8, and 9; and sum-frequency radiation provide by the branched resonator of laser 10 may be collectively referred to as output-radiation.

From the above presented description, those skilled in that art may conceive of resonator arrangements other than those described and depicted without departing from the spirit and scope of the present invention. Accordingly, the present invention is not limited by those embodiments described and depicted. Rather, the invention is depicted by the claims appended hereto.

What is claimed is:

1. A pulsed intracavity frequency-converted, solid-state laser, comprising:

a first resonant-cavity including a solid-state gain-medium;

an optical-pump for energizing said solid-state gain-medium thereby causing laser-radiation at a fundamental wavelength to circulate in said first resonant-cavity;

an optically-nonlinear crystal located in said resonant-cavity for converting the frequency of the laser-radiation to create output-radiation having a wavelength different from that of the fundamental wavelength and wherein said laser radiation circulates in said resonant cavity in more than one longitudinal mode; and a power supply for energizing the optical pump, said power supply being operated in such a way that said frequency-converted output-radiation is provided in repeated bursts of output-pulses at a burst-repetition rate between about 1 Hz and 5 Hz, each of said bursts having a duration greater than about 3 milliseconds and including two or more output-pulses having a duration greater than about 0.5 milliseconds whereby the total energy of the output pulses in each burst is greater than the total energy of a single output pulse having a duration as long as the burst.

2. The laser of claim 1, wherein said optically-nonlinear crystal doubles the frequency of said laser-radiation, said output-radiation has a wavelength half of that of the fundamental radiation and said output-pulses are delivered from said first resonant-cavity.

3. The laser of claim 1, wherein said optically-nonlinear crystal converts said laser-radiation into radiation having a signal-component and an idler-component both of which components have a frequency different from the frequency of said laser-radiation, said optically-nonlinear crystal provides optical-gain for said signal-component and said signal-component is selected as said output-radiation.

4. The laser of claim 3, further incorporating a second resonator arranged such said signal-light resonates therein along a path passing through said optically-nonlinear crystal.

5. The laser of claim 1 wherein said gain-medium is Nd:YLF and said first and second wavelengths are respectively about 1053 nanometers and about 1047 nanometers.

6. The laser of claim 1 wherein said gain-medium is Nd:YAG and said first and second wavelengths are respectively about 1064 nm and about 1061 nm.

7. The laser of claim 1 wherein said gain-medium provides optical gain at first, second, and third wavelengths and said etalon additionally has a reflectivity sufficiently high for said third wavelength that on said energizing of said gain-medium generation of laser-radiation at said third wavelength is prevented.

8. The laser of claim 7, wherein said optically-nonlinear crystal is selected and arranged to double the frequency of said laser-radiation having said first wavelength, and said output-radiation has a wavelength of twice said first wavelength.

9. The laser of claim 8, wherein said gain-medium is Nd:YAG and said first second and third wavelengths are respectively about 1064 nanometers, about 1061 nanometers and about 1074 nanometers.

10. The laser of claim 8 wherein said optically-nonlinear crystal is a KTP crystal.

11. A pulsed intracavity frequency-doubled solid-state laser, comprising:

a laser resonant-cavity including a solid-state gain-medium;

an optical-pump for energizing said solid-state gain-medium thereby causing laser-radiation at a fundamental wavelength to circulate in said laser resonant-cavity;

an optically-nonlinear crystal located in said resonant-cavity for doubling the frequency of the laser-radiation to create frequency-doubled radiation having a wavelength one-half that of the fundamental wavelength and wherein said laser radiation circulates in said resonant cavity in more than one longitudinal mode; and a power supply for energizing the optical pump, said power supply being operated in such a way that said frequency-doubled radiation is delivered therefrom as repeated bursts of output-pulses at a burst-repetition rate between about 1 Hz and 5 Hz, each of said bursts having a duration greater than about 3 milliseconds and including two or more output-pulses having a duration greater than about of 0.5 milliseconds whereby the total energy of the output pulses in each burst is greater than the total energy of a single output pulse having a duration as long as the burst.

12. The laser of claim 11 wherein said output-pulses have a peak power greater than about 25 Watts.

13. The laser of claim 11 wherein said gain-medium is selected from a group of gain media consisting of Nd:YAG, and Nd:YLF.

14. The laser of claim 12 wherein said optically-nonlinear crystal is a crystal of a material selected from a group of optically-nonlinear materials consisting of KTP, LBO, CLBO, BBO, RTA, CTA, RTP, KTA, $KNbO_3$, and $LiNbO_3$.

15. The laser of claim 12 wherein said gain-medium is Nd:YAG and said optically-nonlinear crystal is KTP.

16. The laser of claim 12 wherein said fundamental wavelength is about 1064 nanometers and said output-pulses are at a wavelength of about 532 nanometers.

17. The laser of claim 16, further including an etalon located in said resonant-cavity and configured to prevent generation of laser-radiation at wavelengths of about 1061 nanometers and 1074 nanometers.

18. A pulsed intracavity frequency-converted solid-state laser, comprising:

a laser resonant-cavity including a solid-state gain-medium, said gain-medium providing optical gain at least first and second wavelengths;

an optical-pump for energizing said gain-medium;

an etalon located in said resonant-cavity, said etalon configured to have a reflectivity sufficiently low for said first wavelength and sufficiently high for said second wavelength such that on said energizing of said gain-medium only laser-radiation of said first wavelength circulates in said resonant-cavity;

an optically-nonlinear crystal located in said resonant-cavity for converting the frequency of laser-radiation having said first wavelength circulating therein to create output-radiation having a wavelength different from that of said first wavelength and wherein said laser radiation circulates in said resonant cavity in more than one longitudinal mode; and a power supply for energizing the optical pump, said power supply operated in such a way that said output-radiation is delivered therefrom in repeated bursts of output-pulses at a burst-repetition rate between about 1 Hz and 5 Hz, each of said bursts having a duration greater than about 3.0 milliseconds including two or more output-pulses having a duration greater than about of 0.5 milliseconds whereby the total energy of the output pulses in each burst is greater than the total energy of a single output pulse having a duration as long as the burst.

19. The laser of claim 18 wherein said output-pulses have a peak power greater than about 25 Watts.

20. A pulsed intracavity frequency-doubled solid-state laser, comprising:

a laser resonant-cavity including a solid-state gain-medium, said gain-medium being Nd:YAG providing optical gain at wavelength of about 1061, 1064, and 1074 nanometers;

an optical-pump for energizing said gain-medium;

an etalon located in said resonant-cavity, said etalon configured to have a reflectivity sufficiently low at a wavelength of about 1064 nanometers and sufficiently high at wavelengths of about 1061 and about 1074 nanometers such that on said energizing of said gain-medium, only laser-radiation having a wavelength of about 1064 nanometers circulates in said resonant-cavity;

an optically-nonlinear crystal located in said resonant-cavity for doubling the frequency of 1064-nanometer wavelength laser-radiation circulating therein to create output-radiation having a wavelength of about 532 nanometers and wherein said laser radiation circulates in said resonant cavity in more than one longitudinal mode; and a power supply for energizing the optical pump, said power supply being operated in such a way that said output-radiation is delivered therefrom in repeated bursts of output-pulses at a burst-repetition rate between about 1 Hz and 5 Hz, each of said bursts having a duration greater than about 3.0 milliseconds including two or more output-pulses having a duration greater than about of 0.5 milliseconds whereby the total energy of the output pulses in each burst is greater than the total energy of a single output pulse having a duration as long as the burst.

* * * * *